US012605159B2

(12) United States Patent
Bai et al.

(10) Patent No.: US 12,605,159 B2
(45) Date of Patent: Apr. 21, 2026

(54) INTRASACCULAR OCCLUSIVE DEVICES COMPRISING COPPER MATERIALS

(71) Applicant: Covidien LP, Mansfield, MA (US)

(72) Inventors: Zhijun Bai, Aliso Viejo, CA (US); Junwei Li, Irvine, CA (US)

(73) Assignee: Covidien LP, Mansfield, MA (US)

( * ) Notice: Subject to any disclaimer, the term of this patent is extended or adjusted under 35 U.S.C. 154(b) by 79 days.

(21) Appl. No.: 18/631,785

(22) Filed: Apr. 10, 2024

(65) Prior Publication Data

US 2024/0341769 A1 Oct. 17, 2024

Related U.S. Application Data

(60) Provisional application No. 63/496,089, filed on Apr. 14, 2023.

(51) Int. Cl.
*A61B 17/12* (2006.01)
*A61B 17/00* (2006.01)

(52) U.S. Cl.
CPC .. *A61B 17/12113* (2013.01); *A61B 17/00234* (2013.01); *A61B 17/12031* (2013.01); *A61B 17/12145* (2013.01); *A61B 17/1215* (2013.01); *A61B 17/12172* (2013.01); *A61B 17/12177* (2013.01); *A61B 2017/00292* (2013.01); *A61B 2017/00477* (2013.01); *A61B 2017/00778* (2013.01); *A61B 2017/1205* (2013.01)

(58) Field of Classification Search
CPC ... A61B 17/00; A61B 17/12; A61B 17/12113; A61B 17/00234; A61B 17/12031; A61B 17/12145; A61B 17/1215; A61B 2017/00292; A61B 2017/00778
See application file for complete search history.

(56) References Cited

U.S. PATENT DOCUMENTS

| | | |
|---|---|---|
| 6,585,754 B2 | 7/2003 | Wallace et al. |
| 8,142,456 B2 * | 3/2012 | Rosqueta ........... A61B 17/1215 |
| | | 606/157 |
| 2006/0271086 A1 | 11/2006 | Ramzipoor et al. |

(Continued)

FOREIGN PATENT DOCUMENTS

WO 2014145005 A2 9/2014

OTHER PUBLICATIONS

Monika Szewc, et al. "The Role of Zinc and Copper in Platelet Activation and Pathophysiological Thrombus Formation in Patients with Pulmonary Embolism in the Course of SARS-CoV-2 Infection", Biology 2022, 11 752.https://doi.org/10.3390/biology11050752, https://www.mdpi.com/journal/biology.

*Primary Examiner* — Vi X Nguyen
(74) *Attorney, Agent, or Firm* — Fortem IP LLP

(57) ABSTRACT

Occlusion devices are disclosed herein. According to some embodiments, the present technology includes a mesh configured to be positioned within an aneurysm cavity, the mesh having a low-profile configuration for delivery through a catheter to the aneurysm cavity and an expanded configuration for implantation in the aneurysm cavity. The mesh can include a first portion configured to be positioned over the aneurysm neck and a second portion configured to be positioned between the first portion and a dome of the aneurysm. The mesh can include a copper material at the second portion of the mesh, wherein the copper material is configured to promote thrombosis within the aneurysm cavity.

20 Claims, 3 Drawing Sheets

(56) References Cited

U.S. PATENT DOCUMENTS

| | | | |
|---|---|---|---|
| 2008/0119891 A1* | 5/2008 | Miles | A61B 17/12168 |
| | | | 606/213 |
| 2017/0095254 A1 | 4/2017 | Hewitt et al. | |
| 2021/0007755 A1 | 1/2021 | Lorenzo et al. | |

* cited by examiner

INTRASACCULAR OCCLUSIVE DEVICES COMPRISING COPPER MATERIALS

CROSS-REFERENCE TO RELATED APPLICATIONS

This application claims the benefit of and priority to U.S. Provisional Patent Application Ser. No. 63/496,089 filed Apr. 14, 2023, the entire disclosure of which is incorporated by reference herein.

TECHNICAL FIELD

The present technology relates to occlusive devices for treating body lumens. In particular, the present technology is directed to intrasaccular occlusive devices for treating aneurysms.

BACKGROUND

Intracranial saccular aneurysms occur in 1% to 2% of the general population and account for approximately 80% to 85% of non-traumatic subarachnoid hemorrhages. Recent studies show a case fatality rate of 8.3% to 66.7% in patients with subarachnoid hemorrhage. Endovascular treatment of intracranial aneurysms emerged in the 1990s with the advent of the Guglielmi detachable coil system (Boston Scientific, Natick, MA), which includes packing the aneurysm sac with metal coils to reduce or disrupt the flow of blood into the aneurysm, thereby enabling a local thrombus or clot to form which fills and ultimately closes off the aneurysm. The use of coil embolization to treat aneurysms substantially increased after the publication of favorable clinical data, including evidence that disability or death at the 1-year follow-up occurred in 30.9% of patients treated surgically but only 23.5% in patients treated with coil embolization.[4] Similarly, these trials showed the overall morbidity and mortality at 1 year was 12.6% for surgical clipping and 9.8% for endovascular coiling (amongst patients with no prior history of subarachnoid hemorrhage).

Although coiling has proven to have better outcomes than surgical clipping for both ruptured and unruptured aneurysms, treating complex aneurysms using conventional coiling is challenging. This is especially true for wide-necked aneurysms. Coil segments may protrude from the aneurysm sac through the neck of the aneurysm and into the parent vessel, causing serious complications for the patient. To address this, some treatments include temporarily positioning a balloon within the parent vessel across the neck of the aneurysm to prevent the coils from migrating across the neck during delivery. Alternatively, some treatments include permanently positioning a neck-bridging stent within the parent vessel across the neck of the aneurysm to prevent the coils from migrating across the neck during delivery. While balloon-assisted or stent-assisted coiling for wide-neck aneurysms has shown better occlusion rates and lower recurrence than coiling alone, the recanalization rate of treated large/giant aneurysms can be as high as 18.2%. Moreover, the addition of a balloon or stent and its associated delivery system to the procedure increases the time, cost, and complexity of treatment. Deployment of the stent or balloon during the procedure also greatly increases the risk of an intraprocedural clot forming, and can damage the endothelial lining of the vessel wall. Permanently positioning a stent within the parent vessel increases the chronic risk of clot formation on the stent itself and associated ischemic complications, and thus necessitates the use of dual anti-platelet therapy ("DAPT"). DAPT, in turn, increases the risk and severity of hemorrhagic complications in patients with acutely ruptured aneurysms or other hemorrhagic risks. Thus, neck-bridging stents are not indicated for the treatment of ruptured aneurysms.

The above-noted drawbacks associated with balloon- and stent-assisted coiling techniques influenced the development of intraluminal flow diverting stents, or stent-like structures implanted in the parent vessel across the neck of the aneurysm that redirect blood flow away from the aneurysm, thereby promoting aneurysm thrombosis. Flow diverters have been successfully used for treating wide-neck, giant, fusiform, and blister-like aneurysms. However, because they are positioned in the parent vessel, flow diverters require DAPT to avoid clot formation on the stent itself and ischemic complications. This, in turn, increases the risk and severity of hemorrhagic complications in patients with acutely ruptured aneurysms or other hemorrhagic risks. Thus, flow diverters are not indicated for the treatment of ruptured aneurysms. Flow diverters have also shown limited efficacy in treating bifurcation aneurysms (35-50%).

Endosaccular flow disrupting devices have been gaining momentum over the last decade, generally driven by their potential to provide the intra-aneurysmal flow disruption of coiling with the definitive remodeling at the aneurysm-parent vessel interface achieved by intraluminal flow diverters. Currently existing endosaccular devices are typically mesh devices configured to be deployed completely within the aneurysm sac, with the interstices of the mesh covering the aneurysm neck and reconstructing the aneurysm-parent vessel interface. The implant disrupts the blood flow entering and exiting the aneurysm sac (resulting in stasis and thrombosis) and supports neoendothelial overgrowth without requiring DAPT (unlike endoluminal flow diverters). Thus, endosaccular devices can be used to treat wide-necked aneurysms and ruptured aneurysms. Moreover, because the device is placed completely within the aneurysm sac, the parent and branch vessels are unimpeded and can be accessed for any further retreatment or subsequent deployment of adjunctive devices during treatment.

Accordingly, there is a need for improved devices and methods for treating aneurysms.

SUMMARY

The present technology is directed generally to devices, systems, and methods for the treatment of vascular defects, and in particular, to endosaccular occlusive devices for treating ruptured and un-ruptured intracranial wide-neck, bifurcation, and sidewall aneurysms. The subject technology is illustrated, for example, according to various aspects described below, including with reference to FIGS. 1-5. Various examples of aspects of the subject technology are described as numbered clauses (1, 2, 3, etc.) for convenience. These are provided as examples and do not limit the subject technology.

Example 1: An occlusive device for treating an aneurysm, the device comprising: a mesh configured to be positioned within an aneurysm cavity, the mesh having a low-profile configuration for delivery through a catheter to the aneurysm cavity and an expanded configuration for implantation in the aneurysm cavity, wherein the mesh comprises a first portion configured to be positioned over the aneurysm neck and a second portion configured to be positioned between the first portion and a dome of the aneurysm, wherein the mesh comprises a copper material at the second portion of the mesh, and wherein the copper material is configured to promote thrombosis within the aneurysm cavity.

Example 2: The occlusive device of Example 1, wherein the copper material is a metal alloy that comprises greater than 60% copper.

Example 3: The occlusive device of Example 1 or Example 2, wherein the first portion of the mesh does not include the copper material.

Example 4: The occlusive device of any one of the preceding Examples, wherein the copper material is disposed at an outer region of the second portion to promote thrombosis within the aneurysm cavity between the second portion of the mesh and the dome of the aneurysm.

Example 5; The occlusive device of any one of the preceding Examples, wherein the mesh is defined by a sidewall that surrounds an interior cavity when the mesh is in the expanded configuration, the sidewall having (a) an outer surface facing an inner surface of the aneurysm wall, and (b) an inner surface facing the interior cavity of the mesh, and wherein the copper material is disposed on the outer surface at the second portion to promote thrombosis within the aneurysm cavity between the second portion of the mesh and the dome of the aneurysm.

Example 6: The occlusive device of Example 5, wherein the copper material is a component of a coating disposed on the outer surface at the second portion.

Example 7: The occlusive device of Example 5, wherein the copper material is a thin film disposed on the outer surface at the second portion.

Example 8: The occlusive device of any one of the preceding Examples, wherein the mesh is defined by a sidewall that surrounds an interior cavity when the mesh is in the expanded configuration, the sidewall having (a) an outer surface facing an inner surface of the aneurysm wall, and (b) an inner surface facing the interior cavity of the mesh, and wherein the copper material is disposed on the inner surface to promote thrombosis at least within the interior cavity of the mesh.

Example 9: The occlusive device of Example 8, wherein the copper material is a component of a coating disposed on the inner surface at the second portion.

Example 10: The occlusive device of Example 8, wherein the copper material is a thin film disposed on the inner surface at the second portion.

Example 11: The occlusive device of any one of the previous Examples, wherein the mesh comprises a plurality of braided filaments.

Example 12: The occlusive device of Example 11, wherein: the plurality of braided filaments are secured relative to one another at a coupler disposed at the second portion of the mesh, the coupler comprising the copper material, and at least a portion of the coupler is positioned at an outer region of the second portion to promote thrombosis within the aneurysm cavity between the second portion of the mesh and the dome of the aneurysm.

Example 13: The occlusive device of Example 11 or Example 12 wherein: the mesh is defined by a sidewall that surrounds an interior cavity when the mesh is in the expanded configuration, the plurality of braided filaments are secured relative to one another at a coupler disposed at the second portion of the mesh, the coupler comprising the copper material, and at least a portion of the coupler is positioned within the interior cavity of the mesh to promote thrombosis within the interior cavity of the mesh.

Example 14: The occlusive device of any one of Examples 11 to 13, wherein: the plurality of braided filaments are secured relative to one another at a coupler disposed at the second portion of the mesh, the coupler comprising the copper material, and the occlusive device comprises a flexible member coupled to the coupler and extending away from the coupler and terminating at an outer region of the mesh to promote thrombosis within the aneurysm cavity between the second portion of the mesh and the dome of the aneurysm.

Example 15: The occlusive device of any one of Examples 11 to 14, wherein: the mesh is defined by a sidewall that surrounds an interior cavity when the mesh is in the expanded configuration, the plurality of braided filaments are secured relative to one another at a coupler disposed at the second portion of the mesh, the coupler comprising the copper material, and the occlusive device comprises a flexible member coupled to the coupler and extending away from the coupler into the interior cavity to promote thrombosis within the interior cavity of the mesh.

Example 16: The occlusive device of Example 14 or 15, wherein the flexible member is a coil.

Example 17: The occlusive device of any one of Examples 14 to 16, wherein the flexible member is a plurality of flexible members.

Example 18: The occlusive device of any one of the previous Examples, wherein the copper material comprises a plurality of filaments that are adhered to the second portion of the mesh such that at least a portion of the filaments are exposed at the outer surface of the second portion.

Example 19: The occlusive device of Example 18, wherein the mesh is defined by a sidewall comprising a plurality of pores, and wherein the filaments are woven through the pores of the sidewall along the second portion.

Example 20: A method for treating an aneurysm, the method comprising: positioning a mesh within an aneurysm cavity, the mesh having a low-profile configuration for delivery through a catheter to the aneurysm cavity and an expanded configuration for implantation in the aneurysm cavity, wherein positioning the mesh comprises positioning a first portion of the mesh over the aneurysm neck and a second portion of the mesh between the first portion and a dome of the aneurysm, and wherein the mesh comprises a copper material at the second portion of the mesh, the copper material comprising at least 60% copper such that the copper material promotes thrombosis within the aneurysm cavity.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

The present technology relates to occlusive implants for treating aneurysms. Some embodiments of the present technology, for example, are directed to a mesh configured to be positioned within an aneurysm cavity, the mesh having a low-profile configuration for delivery through a catheter to the aneurysm cavity and an expanded configuration for implantation in the aneurysm cavity. The mesh may comprise a first portion configured to be positioned over the aneurysm neck and a second portion configured to be positioned between the first portion and a dome of the aneurysm. The mesh can include a copper material at the second portion to promote thrombosis within the aneurysm cavity. The thrombogenic response amplified by the copper material advantageously aids the mesh in occluding the aneurysm, thereby reducing and/or eliminating the need to add volume-filling materials to the mesh, such as embolic coils and/or a liquid embolic, as well as expediting healing of the aneurysm.

While the role of copper in thrombosis is complex and not fully understood, the present inventors believe copper ions can generate reactive oxygen species in the body, which can damage cells and tissues and trigger an inflammatory response. Chronic inflammation is known to increase the risk of thrombosis by promoting the formation of blood clots. Another way copper can contribute to thrombosis is by affecting the coagulation cascade, a series of chemical reactions that leads to the formation of blood clots. Copper can enhance the activity of certain clotting factors, such as factor V and fibrinogen, which can increase the risk of thrombosis.

Figure 1:
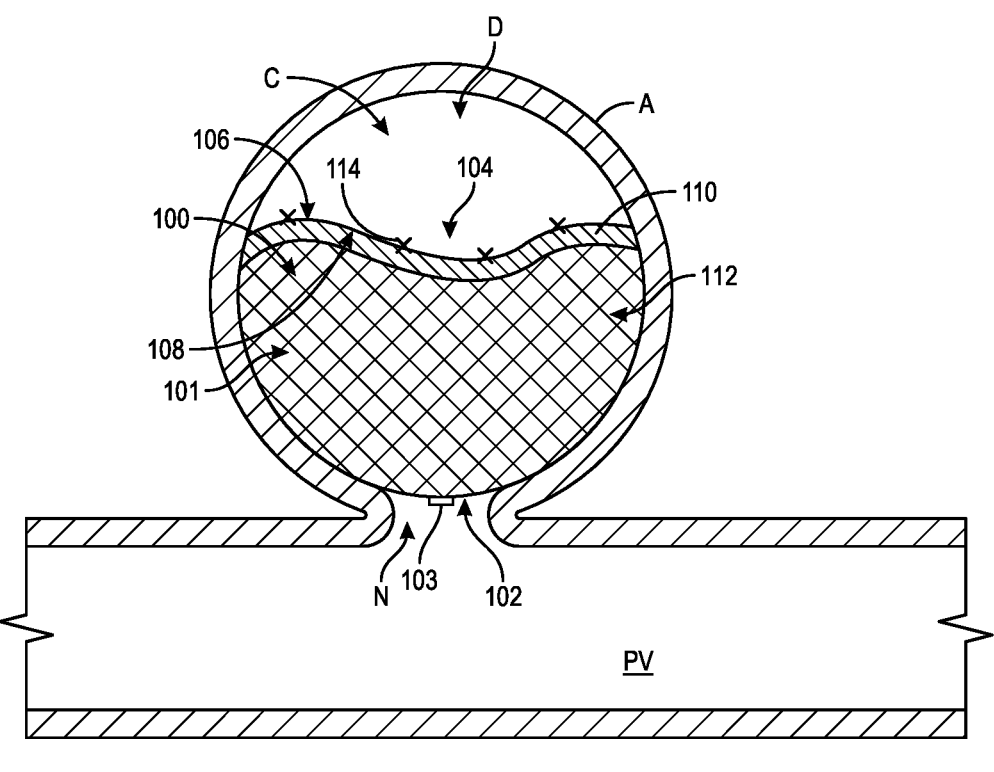
FIG. 1 shows an occlusion device configured in accordance with several embodiments of the present technology, shown positioned within an aneurysm.

FIG. 1 shows an occlusion device 100 in accordance with some embodiments of the present technology shown positioned inside an aneurysm A. The occlusion device 100 can comprise a mesh structure 101 having a low-profile state (not shown) for intravascular delivery to an aneurysm (e.g., a cerebral aneurysm) and an expanded state in which the mesh structure 101 is configured to be positioned within the interior cavity C of the aneurysm. The mesh structure 101 can be shape set to assume a predetermined shape in the expanded state in which the mesh structure 101 contacts and conforms to at least a portion of an inner surface of the aneurysm wall, as shown in FIG. 1. Example shapes include a globular shape, such as a sphere, a prolate spheroid, an oblate spheroid, a bowl, a disc, and others. In the expanded state, the mesh structure 101 can enclose an interior region 112.

As shown in FIG. 1, the mesh structure 101 can include a first portion 102 configured to be positioned over the aneurysm neck N and a second portion 104 configured to be positioned between the first portion 102 and a dome D of the aneurysm A. The mesh structure 101 can have an outer surface 106 that faces away from the interior region 112 (e.g., towards the aneurysm wall) of the mesh structure 101 and an inner surface 108 that faces towards the interior region 112.

The mesh structure 101 may be formed of metal wires, polymer wires, or both, and the wires may have shape memory and/or superelastic properties. The mesh structure 101 may be formed of 24, 32, 36, 48, 64, 72, 96, 128, or 144 filaments. The mesh structure 101 may be formed of a range of filament or wire sizes, such as wires having a diameter of from about 0.0004 inches to about 0.0020 inches, or of from about 0.0009 inches to about 0.0012 inches. In some embodiments, each of the wires or filaments have a diameter of about 0.0004 inches, about 0.0005 inches, about 0.0006 inches, about 0.0007 inches, about 0.0008 inches, about 0.0009 inches, about 0.001 inches, about 0.0011 inches, about 0.0012 inches, about 0.0013 inches, about 0.0014 inches, about 0.0015 inches, about 0.0016 inches, about 0.0017 inches, about 0.0018 inches, about 0.0019 inches, or about 0.0020 inches. In some embodiments, all of the filaments of the braided mesh structure 101 may have the same diameter. For example, in some embodiments, all of the filaments have a diameter of about 0.001 inches. In some embodiments, some of the filaments may have different cross-sectional diameters. For example, some of the filaments may have a slightly thicker diameter to impart additional strength to the braided layers. In some embodiments, some of the filaments can have a diameter of about 0.001 inches, and some of the filaments can have a diameter of greater than 0.001 inches. The thicker filaments may impart greater strength to the braid without significantly increasing the device delivery profile, with the thinner wires offering some strength while filling out the braid matrix density. In some embodiments, the occlusion device 100 includes a connector, such as a metal band, at one or both ends of the mesh structure 101 to hold together the ends of the filaments.

As shown in FIG. 1, the occlusion device 100 can include a coupler 103 configured to be detachably coupled to a delivery system (not shown). In some embodiments, the coupler 103 is positioned at the first portion 102 of the mesh structure 101 (e.g., at the neck N of the aneurysm A when the occlusion device 100 is implanted within the aneurysm A). In some embodiments, the coupler 103 is not disposed at the first portion 102, and instead resides along the second portion 104 (see, for example, FIGS. 3, 4, and 5).

The mesh structure 101 can comprise a copper material at the second portion 104 that is configured to promote thrombosis within the aneurysm cavity. As used herein, "copper material" refers to any metal alloy that comprises at least 50% copper, at least 60% copper, at least 70% copper, at least 80%, or at least 90% copper by weight. In some embodiments, the mesh structure 101 comprises a film 110 of copper material deposited on a surface of the mesh structure 101 (e.g., via electroplating, sputtering, etc.) along the second portion 104. The film can be deposited on the outer surface 106 of the mesh structure 101 at the second portion 104 (as shown in FIG. 1), on the inner surface 108 of the mesh structure 101 at the second portion 104, or both. While copper is an essential nutrient that plays many important roles in the body, too much copper within the bloodstream can be toxic. In order to minimize and/or prevent exposure of the copper material to blood flowing through the parent vessel PV, the mesh structure 101 does not include a copper material at the first portion 102.

In addition to or instead of the mesh structure 101 including a film of copper material, the mesh structure 101 can comprise one or more copper elements (each comprising a copper material) integrated into the mesh structure 101 at the second portion 104. For example, the mesh structure 101 can include one or more filaments comprising a copper material woven into or otherwise adhered to the mesh structure 101 at the second portion 104 such that the copper material forms a portion of the sidewall of the mesh structure 101 at the second portion 104. Additionally or alternatively, the occlusion device 100 can include one or more filaments 114 (only one labeled) comprising a copper material tied, embedded, or otherwise adhered to the mesh structure 101 at the second portion 104.

In some embodiments, the mesh structure 101 may comprise multiple mesh layers, such as inner and outer layers. In these and other multi-layered embodiments, the copper material can be integrated into and/or applied to one, some, or all of the mesh layers. In some variations, the copper material is only incorporated into the second portion 104 of the most exterior mesh layer. In certain embodiments, the copper material is only incorporated into the second portion 104 of the innermost mesh layer.

Figure 2:
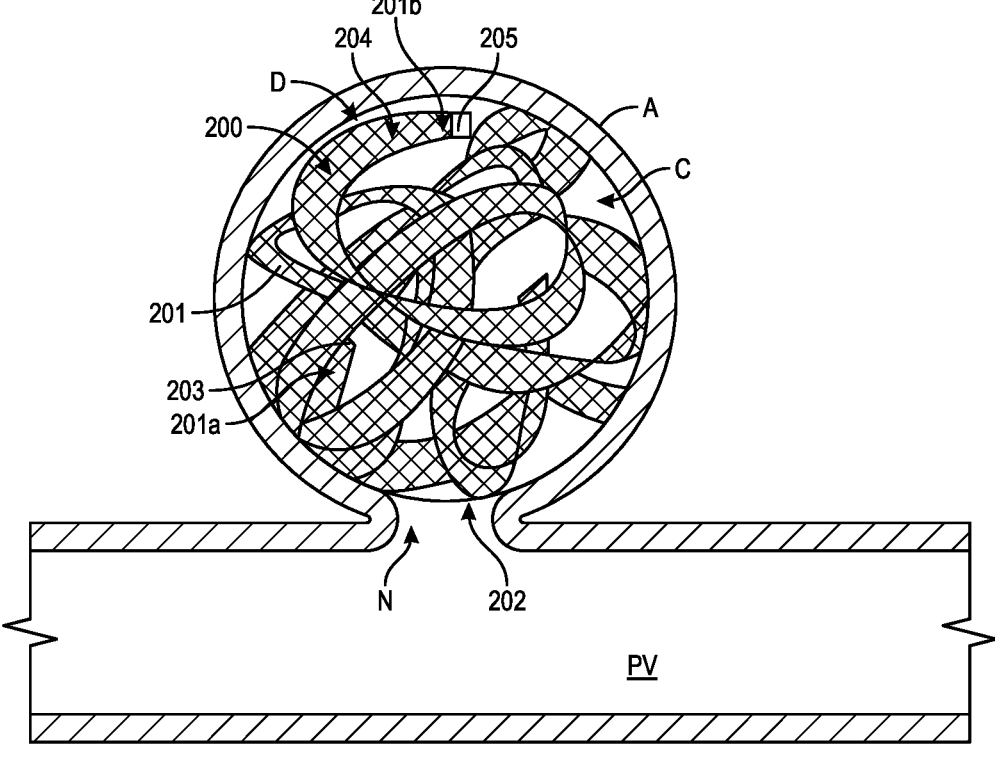
FIG. 2 shows an occlusion device configured in accordance with several embodiments of the present technology, shown positioned within an aneurysm.

FIG. 2 shows an occlusion device 200 in accordance with some embodiments of the present technology shown positioned inside an aneurysm A. The occlusion device 200 can comprise a mesh structure 201 having a low-profile state (not shown) for intravascular delivery to an aneurysm (e.g., a cerebral aneurysm) and an expanded state in which the mesh structure 201 is configured to be positioned within the interior cavity C of the aneurysm. The mesh structure 201 can be formed of a single, continuous mesh ribbon (as shown in FIG. 2), or can comprise a plurality of separate meshes joined end-to-end by one or more coupling elements (e.g., bands, coils, etc.) (not shown). The mesh structure 201 has a first end portion 201*a*, a second end portion 201*b*, and a longitudinal axis extending between the first and second end portions 201*a*, 201*b*. When the occlusion device 200 is positioned within a catheter for delivery to the aneurysm, the second end portion 201*b* of the mesh structure 201 can be positioned distal of the first end portion 201*a* such that the second end portion 201*b* is delivered to the aneurysm cavity C before the first end portion 201*a*.

In some embodiments, such as that shown in FIG. 2, the occlusion device 200 includes a first connector 203 and a second connector 205 coupled to the first and second end portions 201*a*, 201*b*, respectively, of the mesh structure 201. Each of the first and second connectors 203, 205 may comprise, for example, a metal band that collects and holds together the respective ends of the mesh structure 201. The first connector 203 may optionally be configured to detachably couple the occlusion device 200 to a delivery system, and the second connector 205 may optionally be configured to couple a lead-in member (not shown) to the mesh structure 201. The lead-in member can comprise a soft and/or curved element extending distally from the second connector 205. Because the lead-in member is the first portion of the occlusion device 200 that exits the delivery catheter and contacts the aneurysm wall, the soft material and/or curved shape of the lead-in member reduces or eliminates stress on the aneurysm wall when delivering the occlusion device 200 to the aneurysm sac.

In some embodiments, the mesh structure 201 can be formed of a tubular mesh that has been flattened along its longitudinal axis such that opposing portions of the sidewall are pressed against one another and/or into close proximity with one another. In some variations, the mesh structure 201 is formed of a flattened tubular braid. The braid may be formed of a plurality of wires, at least some of which (e.g., 25% of the wires, 50% of the wires, 80% of the wires, 100% of the wires, etc.) are made of one or more shape memory and/or superelastic materials (e.g., Nitinol). In some embodiments, at least some of the plurality of wires may be drawn-filled tubes ("DFT") having a have a radiopaque core (e.g., platinum) surrounded by a shape memory alloy and/or superelastic alloy (e.g., Nitinol). In these and other embodiments, at least a portion of the wires can be made of other suitable materials, such as stainless steel, a cobalt chromium alloy, and others.

As shown in FIG. 2, when the occlusion device 200 is implanted within the aneurysm cavity C, at least a first portion 202 of the mesh structure 201 is positioned over the aneurysm neck N and a second portion 204 of the mesh structure 201 is positioned between the first portion 202 and a dome D of the aneurysm A. The mesh structure 201 can comprise a copper material at the second portion 204 to promote thrombosis within the aneurysm cavity. For the reasons previously mentioned, the mesh structure 201 does not include a copper material at the first portion 202. In some embodiments, the occlusion device 200 comprises a film deposited on the surface of the mesh structure 201 (e.g., via electroplating, sputtering, etc.) along the second portion 204. In these and other embodiments, the mesh structure 201 can comprise one or more copper elements (each comprising a copper material) integrated into the mesh structure 201 at the second portion 204. For example, the copper element can comprise a copper wire that is woven into or otherwise adhered to the mesh structure 201 at the second portion 204. It may be beneficial for the second portion 204 of the mesh structure 201 to be closer to the second end portion 201*b* of the mesh structure 201 than the first end portion 201*a* to ensure that the copper material of the second portion 204 is positioned at an interior region of the aneurysm cavity C or near the dome D of the aneurysm A, away from the neck N of the aneurysm and parent vessel PV.

In some embodiments, the second connector 205 can optionally comprise a copper material. For example, in those embodiments in which the second connector 205 comprises a metal band, the band may be formed of a copper material. Additionally or alternatively, the band may include a film deposited on the surface of the mesh structure 201 (e.g., via electroplating, sputtering, etc.), where the film comprises a copper material.

In some embodiments, the mesh structure 201 may not have a pre-defined shape in the expanded state. In other embodiments, the mesh structure 201 may define a predetermined three-dimensional shape, such as the spherical shape shown in FIG. 2. Depending on the geometry of the aneurysm to be treated, the predetermined shape delimited by the mesh structure 201 can be selected from a variety of spherical or non-spherical shapes, including cylinders, hemispheres, noodles, polyhedrons (e.g., cuboids, tetrahedrons (e.g. pyramids), octahedrons, prisms, etc.), prolate spheroids, oblate spheroids, plates (e.g., discs, polygonal plates), bowls, non-spherical surfaces of revolution (e.g., toruses, cones, cylinders, or other shapes rotated about a center point or a coplanar axis), and combinations thereof.

Figure 3:
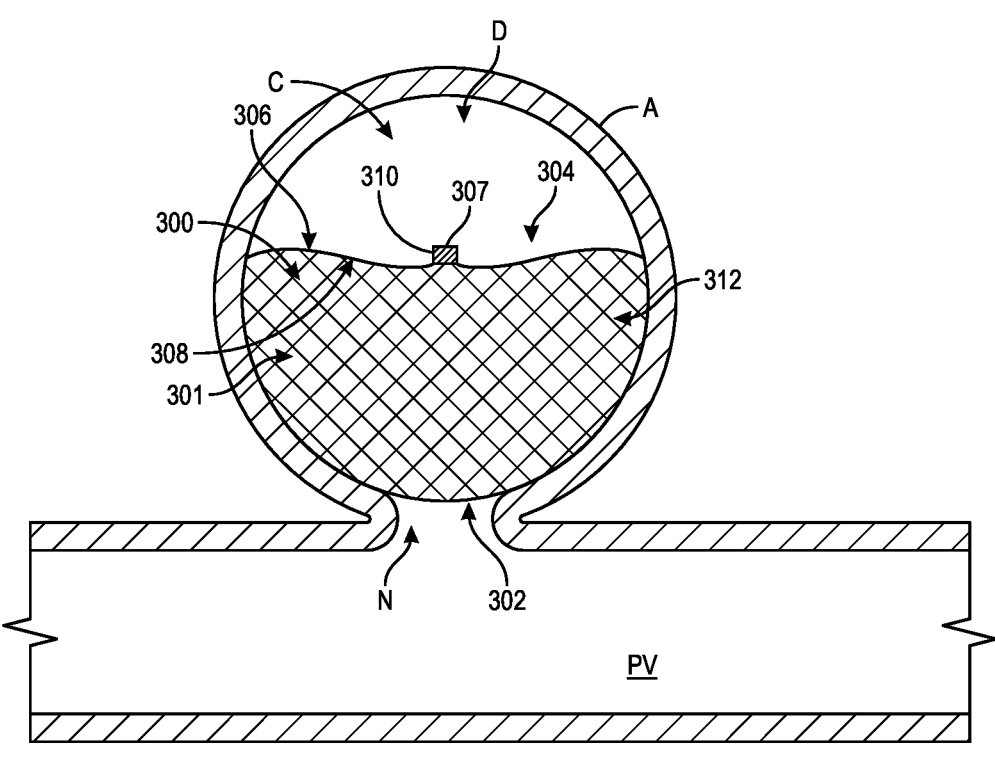
FIG. 3 shows an occlusion device configured in accordance with several embodiments of the present technology, shown positioned within an aneurysm.

FIG. 3 shows an occlusion device 300 in accordance with some embodiments of the present technology shown positioned inside an aneurysm A. The occlusion device 300 can comprise a mesh structure 301 having a low-profile state (not shown) for intravascular delivery to an aneurysm (e.g., a cerebral aneurysm) and an expanded state in which the mesh structure 301 is configured to be positioned within the interior cavity C of the aneurysm. The mesh structure 301 can be shape set to assume a predetermined shape in the expanded state in which the mesh structure 301 contacts and conforms to at least a portion of the inner surface of the aneurysm wall, as shown in FIG. 3. Example shapes include a globular shape, such as a sphere, a prolate spheroid, an oblate spheroid, a bowl, a disc, and others. In the expanded state, the mesh structure 301 can enclose an interior region 312.

As shown in FIG. 3, the mesh structure 301 can include a first portion 302 configured to be positioned over the aneurysm neck N and a second portion 304 configured to be positioned between the first portion 302 and a dome D of the aneurysm A. The mesh structure 301 can have an outer surface 306 that faces away from the interior region 312

(e.g., towards the aneurysm wall) of the mesh structure 301 and an inner surface 308 that faces towards the interior region 312.

The mesh structure 301 may be formed of metal wires, polymer wires, or both, and the wires may have shape memory and/or superelastic properties. The mesh structure 301 may be formed of 24, 32, 36, 48, 64, 72, 96, 128, or 144 filaments. The mesh structure 301 may be formed of a range of filament or wire sizes, such as wires having a diameter of from about 0.0004 inches to about 0.0020 inches, or of from about 0.0009 inches to about 0.0012 inches. In some embodiments, each of the wires or filaments have a diameter of about 0.0004 inches, about 0.0005 inches, about 0.0006 inches, about 0.0007 inches, about 0.0008 inches, about 0.0009 inches, about 0.001 inches, about 0.0011 inches, about 0.0012 inches, about 0.0013 inches, about 0.0014 inches, about 0.0015 inches, about 0.0016 inches, about 0.0017 inches, about 0.0018 inches, about 0.0019 inches, or about 0.0020 inches. In some embodiments, all of the filaments of the braided mesh structure 301 may have the same diameter. For example, in some embodiments, all of the filaments have a diameter of about 0.001 inches. In some embodiments, some of the filaments may have different cross-sectional diameters. For example, some of the filaments may have a slightly thicker diameter to impart additional strength to the braided layers. In some embodiments, some of the filaments can have a diameter of about 0.001 inches, and some of the filaments can have a diameter of greater than 0.001 inches. The thicker filaments may impart greater strength to the braid without significantly increasing the device delivery profile, with the thinner wires offering some strength while filling out the braid matrix density. In some embodiments, the occlusion device 300 includes a connector, such as a metal band, at one or both ends of the mesh structure 301 to hold together the ends of the filaments.

As shown in FIG. 3, the occlusion device 300 can include a connector 307 at the second portion 304 of the mesh structure 301 (e.g., within the aneurysm cavity C and away from the neck N of the aneurysm A). In some embodiments, the connector 307 can be configured to hold together the filaments of the braid of the mesh structure 301. For example, the connector 307 can be a metal band, a weld, etc. In some variations, the connector 307 is optionally configured to be detachably coupled to a delivery system (not shown). In other variations, the mesh structure 301 includes a separate coupler (not shown) at the first portion 302 that is configured to be detachably coupled to a delivery system. In any case, the connector 307 comprises a copper material configured to promote thrombosis within the aneurysm cavity. In some embodiments, the connector 307 includes a film 310 of copper material deposited on an outer surface of the connector 307 (e.g., via electroplating, sputtering, etc.). For the reasons previously mentioned, the mesh structure 301 does not include a copper material at the first portion 302.

In addition to or instead of the connector 307 including the copper material, the mesh structure 301 can comprise one or more copper elements (each comprising a copper material) integrated into the mesh structure 301 at the second portion 304, as described above with reference to FIG. 1. Additionally or alternatively, the occlusion device 300 can include one or more filaments (not shown) comprising a copper material tied, embedded, or otherwise adhered to the mesh structure 301 at the second portion 304, also as described above with reference to FIG. 1.

The mesh structure 301 may comprise multiple mesh layers, such as inner and outer layers. In these and other multi-layered embodiments, the copper material can be integrated into and/or applied to one, some, or all of the mesh layers. In some variations, the copper material is only incorporated into the second portion 304 of the most exterior mesh layer. In certain embodiments, the copper material is only incorporated into the second portion 304 of the innermost mesh layer.

Figure 4:
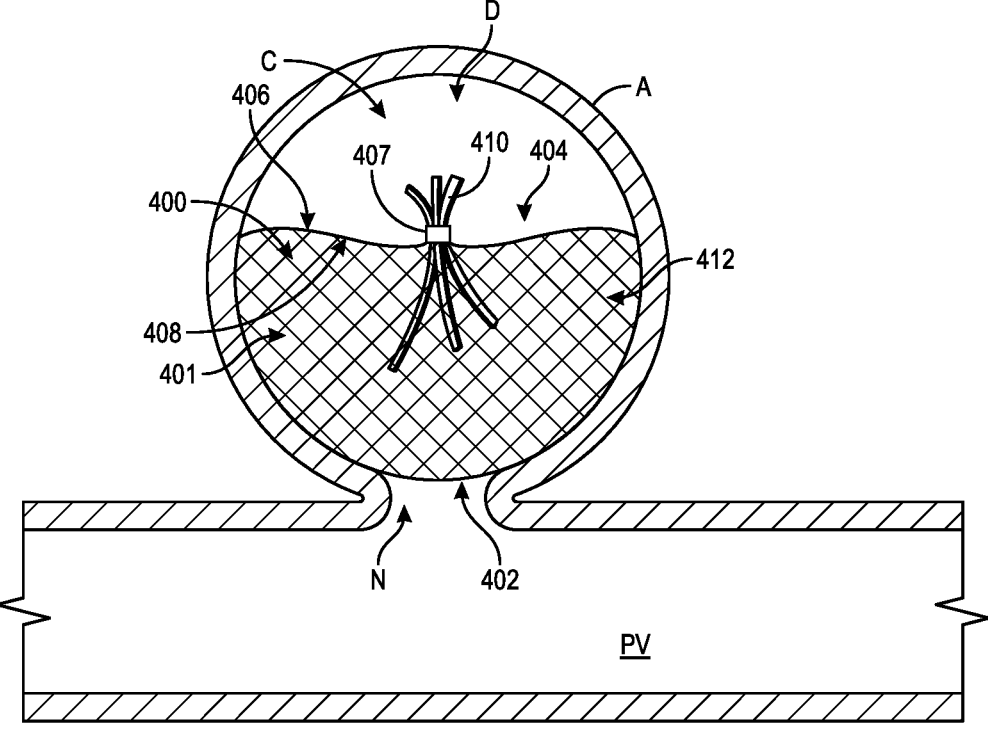
FIG. 4 shows an occlusion device configured in accordance with several embodiments of the present technology, shown positioned within an aneurysm.

FIG. 4 shows an occlusion device 400 in accordance with some embodiments of the present technology shown positioned inside an aneurysm A. The occlusion device 400 can comprise a mesh structure 401 having a low-profile state (not shown) for intravascular delivery to an aneurysm (e.g., a cerebral aneurysm) and an expanded state in which the mesh structure 401 is configured to be positioned within the interior cavity C of the aneurysm. The mesh structure 401 can be shape set to assume a predetermined shape in the expanded state in which the mesh structure 401 contacts and conforms to at least a portion of the inner surface of the aneurysm wall, as shown in FIG. 4. Example shapes include a globular shape, such as a sphere, a prolate spheroid, an oblate spheroid, a bowl, a disc, and others. In the expanded state, the mesh structure 401 can enclose an interior region 412.

As shown in FIG. 4, the mesh structure 401 can include a first portion 402 configured to be positioned over the aneurysm neck N and a second portion 404 configured to be positioned between the first portion 402 and a dome D of the aneurysm A. The mesh structure 401 can have an outer surface 406 that faces away from the interior region 412 (e.g., towards the aneurysm wall) of the mesh structure 401 and an inner surface 408 that faces towards the interior region 412.

The mesh structure 401 may be formed of metal wires, polymer wires, or both, and the wires may have shape memory and/or superelastic properties. The mesh structure 401 may be formed of 24, 32, 36, 48, 64, 72, 96, 128, or 144 filaments. The mesh structure 401 may be formed of a range of filament or wire sizes, such as wires having a diameter of from about 0.0004 inches to about 0.0020 inches, or of from about 0.0009 inches to about 0.0012 inches. In some embodiments, each of the wires or filaments have a diameter of about 0.0004 inches, about 0.0005 inches, about 0.0006 inches, about 0.0007 inches, about 0.0008 inches, about 0.0009 inches, about 0.001 inches, about 0.0011 inches, about 0.0012 inches, about 0.0013 inches, about 0.0014 inches, about 0.0015 inches, about 0.0016 inches, about 0.0017 inches, about 0.0018 inches, about 0.0019 inches, or about 0.0020 inches. In some embodiments, all of the filaments of the braided mesh structure 401 may have the same diameter. For example, in some embodiments, all of the filaments have a diameter of about 0.001 inches. In some embodiments, some of the filaments may have different cross-sectional diameters. For example, some of the filaments may have a slightly thicker diameter to impart additional strength to the braided layers. In some embodiments, some of the filaments can have a diameter of about 0.001 inches, and some of the filaments can have a diameter of greater than 0.001 inches. The thicker filaments may impart greater strength to the braid without significantly increasing the device delivery profile, with the thinner wires offering some strength while filling out the braid matrix density. In some embodiments, the occlusion device 400 includes a connector, such as a metal band, at one or both ends of the mesh structure 401 to hold together the ends of the filaments.

As shown in FIG. 4, the occlusion device 400 can include a connector 407 at the second portion 404 of the mesh structure 401 (e.g., within the aneurysm cavity C and away from the neck N of the aneurysm A). In some embodiments, the connector 407 can be configured to hold together the filaments of the braid of the mesh structure 401. For example, the connector 407 can be a metal band, a weld, etc. In some variations, the connector 407 is optionally configured to be detachably coupled to a delivery system (not shown). In other variations, the mesh structure 401 includes a separate coupler (not shown) at the first portion 402 that is configured to be detachably coupled to a delivery system.

In any case, the occlusion device 400 can further include one or more copper elements 410 (each comprising a copper material) coupled to and extending away from the connector 407. In some embodiments, one, some, or all of the copper elements 410 can extend away from the connector 407 into a space within the aneurysm cavity C between an exterior region of the mesh structure 401 and a dome D of the aneurysm A, thereby promoting thrombosis within the space. Additionally or alternatively, one, some, or all of the copper elements 410 can extend away from the connector 407 into the interior region 412 of the mesh structure 401, thereby promoting thrombosis within the interior region 412. In such embodiments, the copper element(s) 410 can have a length sufficiently short to avoid placement of an end of a copper element 410 near the first portion 402 of the mesh structure 401 and/or neck N of the aneurysm A when the occlusion device 400 is implanted. The occlusion device 400 can include copper element(s) that only extend distally from the connector 407 into the space between the mesh structure 401 and the dome D of the aneurysm, copper element(s) that extend proximally from the connector 407 into the interior region of the mesh structure 401, and/or copper element(s) that extend both distally and proximally (as shown in FIG. 4).

In addition to the copper elements 410, the connector 407 can include a film of copper material deposited on an outer surface of the connector 407 (e.g., via electroplating, sputtering, etc.), for example as described above with reference to FIG. 3. Additionally or alternatively, the mesh structure 401 can comprise one or more copper elements (each comprising a copper material) integrated into the mesh structure 401 at the second portion 404, as described above with reference to FIG. 1. Additionally or alternatively, the occlusion device 400 can include one or more filaments (not shown) comprising a copper material tied, embedded, or otherwise adhered to the mesh structure 401 at the second portion 404, also as described above with reference to FIG. 1.

The mesh structure 401 may comprise multiple mesh layers, such as inner and outer layers. In these and other multi-layered embodiments, the copper material can be integrated into and/or applied to one, some, or all of the mesh layers. In some variations, the copper material is only incorporated into the second portion 404 of the most exterior mesh layer. In certain embodiments, the copper material is only incorporated into the second portion 404 of the innermost mesh layer.

Figure 5:
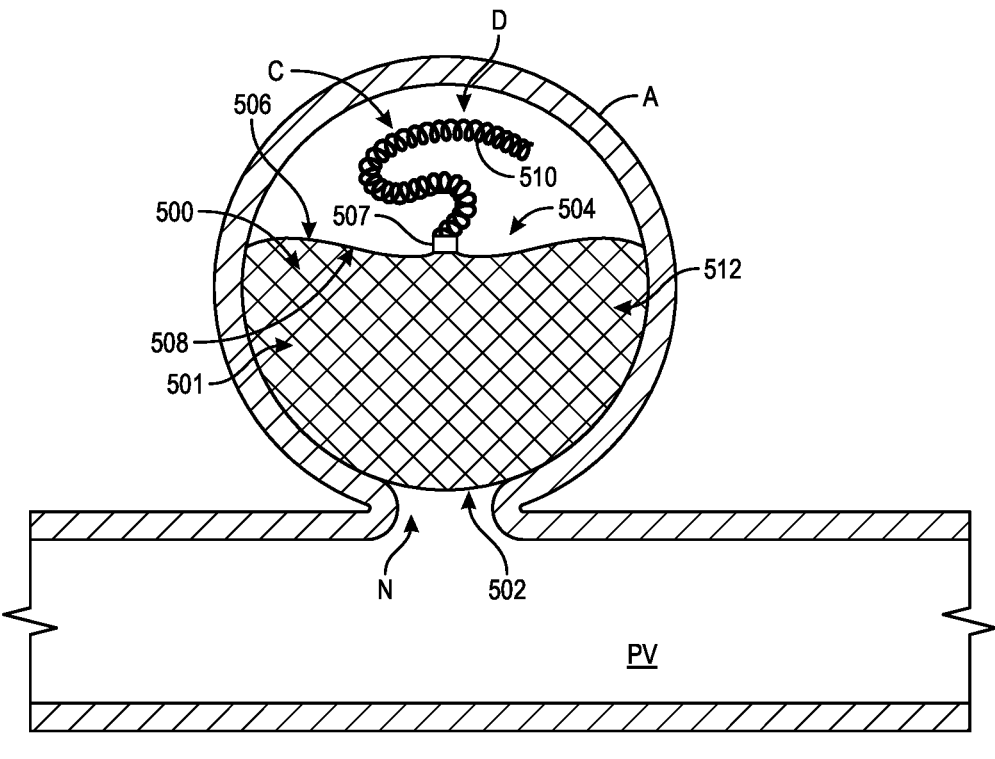
FIG. 5 shows an occlusion device configured in accordance with several embodiments of the present technology, shown positioned within an aneurysm.

FIG. 5 shows an occlusion device 500 in accordance with some embodiments of the present technology shown positioned inside an aneurysm A. The occlusion device 500 can comprise a mesh structure 501 having a low-profile state (not shown) for intravascular delivery to an aneurysm (e.g., a cerebral aneurysm) and an expanded state in which the mesh structure 501 is configured to be positioned within the interior cavity C of the aneurysm. The mesh structure 501 can be shape set to assume a predetermined shape in the expanded state in which the mesh structure 501 contacts and conforms to at least a portion of the inner surface of the aneurysm wall, as shown in FIG. 5. Example shapes include a globular shape, such as a sphere, a prolate spheroid, an oblate spheroid, a bowl, a disc, and others. In the expanded state, the mesh structure 501 can enclose an interior region 512.

As shown in FIG. 5, the mesh structure 501 can include a first portion 502 configured to be positioned over the aneurysm neck N and a second portion 504 configured to be positioned between the first portion 502 and a dome D of the aneurysm A. The mesh structure 501 can have an outer surface 506 that faces away from the interior region 512 (e.g., towards the aneurysm wall) of the mesh structure 501 and an inner surface 508 that faces towards the interior region 512.

The mesh structure 501 may be formed of metal wires, polymer wires, or both, and the wires may have shape memory and/or superelastic properties. The mesh structure 501 may be formed of 24, 32, 36, 48, 64, 72, 96, 128, or 144 filaments. The mesh structure 501 may be formed of a range of filament or wire sizes, such as wires having a diameter of from about 0.0004 inches to about 0.0020 inches, or of from about 0.0009 inches to about 0.0012 inches. In some embodiments, each of the wires or filaments have a diameter of about 0.0004 inches, about 0.0005 inches, about 0.0006 inches, about 0.0007 inches, about 0.0008 inches, about 0.0009 inches, about 0.001 inches, about 0.0011 inches, about 0.0012 inches, about 0.0013 inches, about 0.0014 inches, about 0.0015 inches, about 0.0016 inches, about 0.0017 inches, about 0.0018 inches, about 0.0019 inches, or about 0.0020 inches. In some embodiments, all of the filaments of the braided mesh structure 501 may have the same diameter. For example, in some embodiments, all of the filaments have a diameter of about 0.001 inches. In some embodiments, some of the filaments may have different cross-sectional diameters. For example, some of the filaments may have a slightly thicker diameter to impart additional strength to the braided layers. In some embodiments, some of the filaments can have a diameter of about 0.001 inches, and some of the filaments can have a diameter of greater than 0.001 inches. The thicker filaments may impart greater strength to the braid without significantly increasing the device delivery profile, with the thinner wires offering some strength while filling out the braid matrix density. In some embodiments, the occlusion device 500 includes a connector, such as a metal band, at one or both ends of the mesh structure 501 to hold together the ends of the filaments.

As shown in FIG. 5, the occlusion device 500 can include a connector 507 at the second portion 504 of the mesh structure 501 (e.g., within the aneurysm cavity C and away from the neck N of the aneurysm A). In some embodiments, the connector 507 can be configured to hold together the filaments of the braid of the mesh structure 501. For example, the connector 507 can be a metal band, a weld, etc. In some variations, the connector 507 is optionally configured to be detachably coupled to a delivery system (not shown). In other variations, the mesh structure 501 includes a separate coupler (not shown) at the first portion 502 that is configured to be detachably coupled to a delivery system.

In any case, the occlusion device 500 can further include one or more coils 510, each comprising a copper material, coupled to and extending away from the connector 507. Some or all of the coils 510 can comprise a helical wire consisting of a copper material, and in some cases some or all of the coils 510 can comprise a helical wire consisting of other metals coated with a copper material or comprising a copper deposited film. In such embodiments where the wire forming the coil consists of other metals, the other metal may or may not include copper, but at a weight percentage less than 50%. In some embodiments, one, some, or all of the coils 510 can extend away from the connector 507 into a space within the aneurysm cavity C between an exterior region of the mesh structure 501 and a dome D of the aneurysm A, thereby promoting thrombosis within the space. Additionally or alternatively, the coils 510 can extend away from the connector 507 into the interior region 512 of the mesh structure 501 (not shown), thereby promoting thrombosis within the interior region 512. In such embodiments, the coils 510 can have a length sufficiently short to avoid placement of an end of a coil 510 near the first portion 502 of the mesh structure 501 and/or neck N of the aneurysm A when the occlusion device 500 is implanted. The occlusion device 500 can include coil(s) that only extend distally from the connector 507 into the space between the mesh structure 501 and the dome D of the aneurysm, coil(s) that extend proximally from the connector 507 into the interior region of the mesh structure 501, and/or coil(s) that extend both distally and proximally (as shown in FIG. 5).

In addition to the coils 510, the occlusion device 500 can optionally have one or more copper elements as described above with reference to FIG. 4. Additionally or alternatively, the connector 507 can include a film of copper material deposited on an outer surface of the connector 507 (e.g., via electroplating, sputtering, etc.), for example as described above with reference to FIG. 3. Additionally or alternatively, the mesh structure 501 can comprise one or more copper elements (each comprising a copper material) integrated into the mesh structure 501 at the second portion 504, as described above with reference to FIG. 1. Additionally or alternatively, the occlusion device 500 can include one or more filaments (not shown) comprising a copper material tied, embedded, or otherwise adhered to the mesh structure 501 at the second portion 504, also as described above with reference to FIG. 1.

The mesh structure 501 may comprise multiple mesh layers, such as inner and outer layers. In these and other multi-layered embodiments, the copper material can be integrated into and/or applied to one, some, or all of the mesh layers. In some variations, the copper material is only incorporated into the second portion 504 of the most exterior mesh layer. In certain embodiments, the copper material is only incorporated into the second portion 504 of the innermost mesh layer.

CONCLUSION

Although many of the embodiments are described above with respect to systems, devices, and methods for occluding cerebral aneurysms, the technology is applicable to other applications and/or other approaches, such as the treatment and/or occlusion of any lumen in any part of the vasculature and/or heart. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1-5.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

As used herein, the terms "generally," "substantially," "about," and similar terms are used as terms of approximation and not as terms of degree, and are intended to account for the inherent variations in measured or calculated values that would be recognized by those of ordinary skill in the art.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. An occlusive device for treating an aneurysm, the device comprising:
   a mesh configured to be positioned within an aneurysm cavity, the mesh having a low-profile configuration for delivery through a catheter to the aneurysm cavity and an expanded configuration for implantation in the aneurysm cavity, wherein the mesh comprises:
      a first portion configured to be positioned over the aneurysm neck and a second portion configured to be positioned between the first portion and a dome of the aneurysm,
      a copper material at the second portion of the mesh and configured to promote thrombosis within the aneurysm cavity, and
      a plurality of braided filaments secured relative to one another at a coupler disposed at the second portion of the mesh, the coupler comprising the copper material, wherein at least a portion of the coupler is positioned at an outer region of the second portion to promote thrombosis within the aneurysm cavity between the second portion of the mesh and the dome of the aneurysm.

2. The occlusive device of claim 1, wherein the copper material is a metal alloy that comprises at least 50% copper by weight.

3. The occlusive device of claim 1, wherein the copper material is a metal alloy that comprises at least 70% copper by weight.

4. The occlusive device of claim 1, wherein the first portion of the mesh does not include the copper material.

5. The occlusive device of claim 1, further comprising a copper material disposed at an outer region of the second portion to promote thrombosis within the aneurysm cavity between the second portion of the mesh and the dome of the aneurysm.

6. An occlusive device for treating an aneurysm, the device comprising:

a mesh configured to be positioned within an aneurysm cavity, the mesh having a low-profile configuration for delivery through a catheter to the aneurysm cavity and an expanded configuration for implantation in the aneurysm cavity, wherein the mesh is defined by a sidewall that surrounds an interior cavity when the mesh is in the expanded configuration, and wherein the mesh comprises:

a first portion configured to be positioned over the aneurysm neck and a second portion configured to be positioned between the first portion and a dome of the aneurysm, a copper material at the second portion of the mesh and configured to promote thrombosis within the aneurysm cavity, and a plurality of braided filaments secured relative to one another at a coupler disposed at the second portion of the mesh, the coupler comprising the copper material, and wherein at least a portion of the coupler is positioned within the interior cavity of the mesh to promote thrombosis within the interior cavity of the mesh.

7. The occlusive device of claim 6, wherein the occlusive device comprises a flexible member coupled to the coupler and extending away from the coupler into the interior cavity to promote thrombosis within the interior cavity of the mesh.

8. The occlusive device of claim 7, wherein the flexible member is a coil.

9. The occlusive device of claim 7, wherein the flexible member is a plurality of flexible members.

10. The occlusive device of claim 6, wherein the copper material is a metal alloy that comprises at least 50% copper.

11. The occlusive device of claim 6, wherein the copper material is a metal alloy that comprises at least 70% copper by weight.

12. The occlusive device of claim 6, wherein the first portion of the mesh does not include the copper material.

13. The occlusive device of claim 6, further comprising a copper material disposed at an outer region of the second portion to promote thrombosis within the aneurysm cavity between the second portion of the mesh and the dome of the aneurysm.

14. An occlusive device for treating an aneurysm, the device comprising:

a mesh configured to be positioned within an aneurysm cavity, the mesh having a low-profile configuration for delivery through a catheter to the aneurysm cavity and an expanded configuration for implantation in the aneurysm cavity, wherein the mesh is defined by a sidewall that surrounds an interior cavity when the mesh is in the expanded configuration, and wherein the mesh comprises:

a first portion configured to be positioned over the aneurysm neck and a second portion configured to be positioned between the first portion and a dome of the aneurysm, a copper material at the second portion of the mesh and configured to promote thrombosis within the aneurysm cavity, and a plurality of braided filaments secured relative to one another at a coupler disposed at the second portion of the mesh, the coupler comprising the copper material; and a flexible member coupled to the coupler and extending away from the coupler and terminating at an outer region of the mesh to promote thrombosis within the aneurysm cavity between the second portion of the mesh and the dome of the aneurysm.

15. The occlusive device of claim 14, wherein the flexible member is a coil.

16. The occlusive device of claim 14, wherein the flexible member is a plurality of flexible members.

17. The occlusive device of claim 14, wherein the copper material is a metal alloy that comprises at least 50% copper.

18. The occlusive device of claim 14, wherein the copper material is a metal alloy that comprises at least 70% copper by weight.

19. The occlusive device of claim 14, wherein the first portion of the mesh does not include the copper material.

20. The occlusive device of claim 14, further comprising a copper material disposed at an outer region of the second portion to promote thrombosis within the aneurysm cavity between the second portion of the mesh and the dome of the aneurysm.

* * * * *